(12) United States Patent
Wendland et al.

(10) Patent No.: US 11,351,304 B2
(45) Date of Patent: Jun. 7, 2022

(54) INJECTION DEVICE

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 244 days.

(21) Appl. No.: 16/328,523

(22) PCT Filed: Aug. 25, 2017

(86) PCT No.: PCT/EP2017/071461
§ 371 (c)(1),
(2) Date: Feb. 26, 2019

(87) PCT Pub. No.: WO2018/041741
PCT Pub. Date: Mar. 8, 2018

(65) Prior Publication Data
US 2019/0184101 A1 Jun. 20, 2019

(30) Foreign Application Priority Data
Aug. 30, 2016 (EP) ..................... 16186287

(51) Int. Cl.
*A61M 5/20* (2006.01)
*A61M 5/32* (2006.01)
(52) U.S. Cl.
CPC ........ *A61M 5/2033* (2013.01); *A61M 5/3232* (2013.01); *A61M 5/3287* (2013.01);
(Continued)

(58) Field of Classification Search
CPC .............. A61M 5/2033; A61M 5/3232; A61M 5/3287; A61M 2005/2006; A61M 2005/206; A61M 5/3272; A61M 2005/208
See application file for complete search history.

(56) References Cited

U.S. PATENT DOCUMENTS 5,232,457 A * 8/1993 Grim ....................... A61M 5/24
604/195
6,544,234 B1 * 4/2003 Gabriel ............... A61M 5/2033
604/134

(Continued)

FOREIGN PATENT DOCUMENTS

| CN | 103492003 | 1/2014 |
| CN | 103920212 | 7/2014 |

(Continued)

OTHER PUBLICATIONS

PCT International Preliminary Report on Patentability in International Appln. No. PCT/EP2017/071461, dated Mar. 5, 2019, 7 pages.

(Continued)

*Primary Examiner* — Bhisma Mehta
*Assistant Examiner* — John J Crawford
(74) *Attorney, Agent, or Firm* — Fish & Richardson P.C.

(57) ABSTRACT

An injection device comprising: a housing arranged to contain a syringe with a piston for sealing the syringe and displacing the medicament, the housing having a proximal end and a distal end, wherein the distal end is intended to be applied against an injection site; a driving mechanism arranged between the piston and the proximal end of the housing; and a locking mechanism comprising a plate member arranged between the driving mechanism and the piston to retain the driving mechanism to retain the driving mechanism in an initial inactive state in which the driving mechanism cannot be actuated; wherein when the locking mecha- (Continued)

nism is released, the driving mechanism can be actuated to push the piston towards the distal end of the housing to displace the medicament.

17 Claims, 9 Drawing Sheets

(52) U.S. Cl.
CPC .............. *A61M 2005/2006* (2013.01); *A61M 2005/206* (2013.01); *A61M 2005/208* (2013.01)

(56) References Cited

U.S. PATENT DOCUMENTS

| | | | | |
|---|---|---|---|---|
| 2013/0317447 A1* | 11/2013 | Cowe | ................ | A61M 5/2033 604/196 |
| 2013/0317479 A1* | 11/2013 | Brereton | ............ | A61M 5/31511 604/506 |
| 2014/0343505 A1* | 11/2014 | Henley | ............... | A61M 5/2033 604/198 |
| 2015/0165129 A1* | 6/2015 | Row | ..................... | A61M 5/482 604/189 |
| 2016/0121050 A1 | 5/2016 | Fabien | | |

FOREIGN PATENT DOCUMENTS

| | | |
|---|---|---|
| CN | 104685210 | 6/2015 |
| CN | 104689426 | 6/2015 |
| CN | 104780962 | 7/2015 |
| CN | 105358194 | 2/2016 |
| CN | 105517597 | 4/2016 |
| CN | 205198611 | 5/2016 |
| CN | 105877814 | 8/2016 |
| CN | 106470718 | 3/2017 |
| EP | 2468328 | 6/2012 |
| EP | 2826506 | 1/2015 |
| JP | 2005-073985 | 3/2005 |
| JP | 2012-232152 | 11/2012 |
| JP | 2013-539678 | 10/2013 |
| JP | 2014-036879 | 2/2014 |
| WO | WO 1993/002725 | 2/1993 |
| WO | WO 2006/106291 | 10/2006 |
| WO | WO 2006/123251 | 11/2006 |
| WO | WO 2011/048422 | 4/2011 |
| WO | WO 2012/045827 | 4/2012 |
| WO | WO 2014/053451 | 4/2014 |
| WO | WO 2014/111332 | 7/2014 |
| WO | WO 2014/198798 | 12/2014 |

OTHER PUBLICATIONS

PCT International Search Report and Written Opinion in International Appln. No. PCT/EP2017/071461, dated Nov. 20, 2017, 9 pages.

* cited by examiner

INJECTION DEVICE

CROSS REFERENCE TO RELATED APPLICATIONS

The present application is the national stage entry of International Patent Application No. PCT/EP2017/071461, filed on Aug. 25, 2017, and claims priority to EP Application No. 16186287.5, filed on Aug. 30, 2016, the entire content of each of which are incorporated herein by reference.

TECHNICAL FIELD

The present disclosure relates to an injection device, and a system including an injection device.

BACKGROUND

Current therapies delivered by means of self-administered injections include drugs for diabetes (both insulin and new GLP-A class drugs), migraine, hormone therapies, anticoagulants etc. Administering an injection is a process which presents a number of risks and challenges for user and healthcare professionals, both mental and physical.

Conventional injection devices typically fall under two categories—manual devices and auto-injectors. In a conventional manual device, a user must provide a force to drive a liquid medicament out of the device, e.g. by depressing a plunger.

Auto-injectors aim to make self-administration of injected therapies easier for users. Auto-injectors are devices which completely or partially replace activities involved in medicament delivery of manual devices. These activities may include removal of a protective syringe cap, insertion of a needle into a patient's skin, injection of the medicament, removal of the needle, shield of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth.

SUMMARY

In some injection devices, a driving mechanism is used for driving a piston in a syringe to push liquid medicament out of the syringe during an injection process. Some injection devices adopt a driving mechanism comprising a spring element that is directly supported by a number of plastic components within the housing of the injection device. Due to this direct contact between the plastic components and the spring element of the driving mechanism, creeping of the plastic components may occur because of the stress caused by the spring force stored in the spring element which reduces the shelf life of the injection devices.

In an aspect of the present disclosure, an injection device is disclosed that includes: a housing arranged to contain a syringe with a piston for sealing the syringe and displacing the medicament, the housing having a proximal end and a distal end, wherein the distal end is intended to be applied against an injection site; a driving mechanism arranged between the piston and the proximal end of the housing; and a locking mechanism comprising a plate member arranged between the driving mechanism and the piston to retain the driving mechanism in an initial inactive state in which the driving mechanism cannot be actuated, wherein when the locking mechanism is released, the plate member becomes separated into at least two parts so as to allow actuation of the driving mechanism to push the piston towards the distal end of the housing to displace the medicament.

The injection device may further comprise a retractable inner sleeve, wherein a part of the plate member of the locking mechanism is connected to the inner sleeve such that when a pulling force acts on the inner sleeve to move it towards a distal direction, the plate member becomes separated.

The injection device may further comprise a removable cap arranged to be removably engaged with the distal end of the housing, and an engagement mechanism for releasably engaging the removable cap with the inner sleeve.

The engagement mechanism may comprise a protrusion at an external surface of the removable cap and a slot at an inner surface of the inner sleeve, wherein the protrusion is arranged to be releasably engaged with the slot by rotation of the removable cap.

The driving mechanism may comprise a housing member which houses a drive spring, the drive spring being in a compressed state when the driving mechanism is in the inactive state, and wherein the drive spring is configured to decompress when the locking mechanism is released so as to push the piston towards the distal end of the housing.

The injection device may further comprise a rib arranged on an inner surface of the housing, wherein the rib is arranged to hold at least a part of the housing member of the driving mechanism when the locking mechanism is released, the rib being further arranged to be actuated so as to release the housing member of the driving mechanism to push the piston towards the distal end.

The locking mechanism may comprise a clamp arranged to clamp the housing member of the driving mechanism in a fixed position in the initial inactive state, wherein the clamp is arranged to be bent by a pushing force to release the housing member such that the driving mechanism can be actuated.

The injection device may further comprise a retractable inner sleeve located adjacent to the clamp, wherein the pushing force is provided by pushing the inner sleeve in the proximal direction of the injection device.

The locking mechanism may comprise a clamp arranged to clamp the housing member of the driving mechanism in a fixed position in the initial inactive state, wherein the clamp is arranged to be released by a pulling force to release the housing member such that the driving mechanism can be actuated.

The injection device may further comprise a retractable inner sleeve located adjacent to the clamp, wherein the clamp is connected to the inner sleeve and the pulling force is provided by pulling the inner sleeve in the distal direction of the injection device.

The locking mechanism may comprise a cotter, a first through-hole at a first side of the housing, a second through-hole at a housing member of the driving mechanism, and a third through-hole at a second side of the housing, the second side being opposite to the first side, wherein the first, second, and third through-holes are aligned such that the cotter can be removably inserted through the housing in a direction perpendicular to a longitudinal axis of the injection device so as to retain the driving mechanism in a fixed position in the initial in active state.

The injection device may contain a liquid medicament.

In a second aspect of the present disclosure, an injection device is disclosed that includes: a housing arranged to contain a syringe with a piston for sealing the syringe and displacing the medicament, the housing having a proximal end and a distal end, wherein the distal end is intended to be applied against an injection site; a driving mechanism arranged between the piston and the proximal end of the housing; and a locking mechanism arranged to retain the driving mechanism in an initial inactive state in which direct contact between the driving mechanism and the piston is prevented and the driving mechanism cannot be actuated.

The injection device may further comprise a retractable inner sleeve.

The injection device may further comprise a removable cap arranged to be removably engaged with the distal end of the housing, and an engagement mechanism for releasably engaging the removable cap with the inner sleeve.

The engagement mechanism may comprise a protrusion at an external surface of the removable cap and a slot at an inner surface of the inner sleeve, wherein the protrusion is arranged to be releasably engaged with the slot by rotation of the removable cap.

The driving mechanism may comprise a housing member which houses a drive spring, the drive spring being in a compressed state when the driving mechanism is in the inactive state, and wherein the drive spring is configured to decompress when the locking mechanism is released so as to push the piston towards the distal end of the housing.

The injection device may further comprise a rib arranged on an inner surface of the housing, wherein the rib is arranged to hold at least a part of the housing member of the driving mechanism when the locking mechanism is released, the rib being further arranged to be actuated so as to release the housing member of the driving mechanism to push the piston towards the distal end.

The locking mechanism may comprise a clamp arranged to clamp the housing member of the driving mechanism in a fixed position in the initial inactive state, wherein the clamp is arranged to be bent by a pushing force to release the housing member such that the driving mechanism can be actuated.

The injection device may further comprise a retractable inner sleeve located adjacent to the clamp, wherein the pushing force is provided by pushing the inner sleeve in the proximal direction of the injection device.

The locking mechanism may comprise a clamp arranged to clamp the housing member of the driving mechanism in a fixed position in the initial inactive state, wherein the clamp is arranged to be released by a pulling force to release the housing member such that the driving mechanism can be actuated.

The injection device may further comprise a retractable inner sleeve located adjacent to the clamp, wherein the clamp is connected to the inner sleeve and the pulling force is provided by pulling the inner sleeve in the distal direction of the injection device.

The locking mechanism may comprise a cotter, a first through-hole at a first side of the housing, a second through-hole at a housing member of the driving mechanism, and a third through-hole at a second side of the housing, the second side being opposite to the first side, wherein the first, second, and third through-holes are aligned such that the cotter can be removably inserted through the housing in a direction perpendicular to a longitudinal axis of the injection device so as to retain the driving mechanism in a fixed position in the initial in active state.

The injection device may contain a liquid medicament.

The present disclosure also provides a system comprising: an injection device as described herein, and an apparatus configured to remove the removable cap from the injection device.

The present disclosure discloses a first method of assembling an injection device. The first method comprises: assembling a driving mechanism that is configured to be held in an inactive state initially by a locking mechanism comprising a plate member arranged between the driving mechanism and the piston to retain the driving mechanism in an initial inactive state in which the driving mechanism cannot be actuated, and assembling the locking mechanism such that it can be released by separating the plate member into at least two parts so as to allow the driving mechanism to be actuated to push a piston in a syringe so as to displace medicament contained in the syringe.

The present disclosure discloses a second method of assembling an injection device. The second method comprises: assembling a driving mechanism that is configured to be helf in an inactive state initially by a locking mechanism arranged to retain the driving mechanism in an initial inactive state in which direct contact between the driving mechanism and the piston is prevented and the driving mechanism cannot be actuated, and assembling the locking mechanism such that it can be released to allow the driving mechanism to be actuated to push a piston in a syringe so as to displace medicament contained in the syringe.

These and other aspects of the invention will be apparent from and elucidated with reference to the embodiments described hereinafter.

BRIEF DESCRIPTION OF THE DRAWINGS

Exemplary embodiments of the present invention are described with reference to the accompanying drawings, in which.

The like reference numerals in the drawings refer to like elements throughout.

DETAILED DESCRIPTION

Figure 1A:
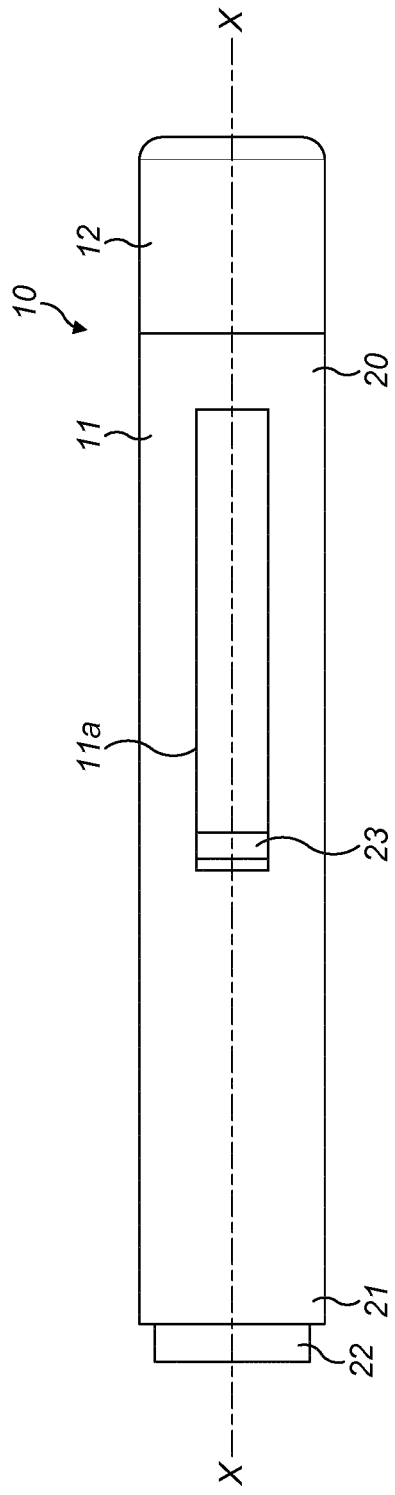
FIGS. 1A and 1B illustrate side views of an injection device according to an embodiment of the present disclosure.

An injection device with an arrangement for activating a driving mechanism is provided. The injection device comprises a housing arranged to contain a syringe with a piston for sealing the syringe and displacing the medicament, the housing having a proximal end and a distal end, wherein the distal end is intended to be applied against an injection site; a driving mechanism arranged between the piston and the proximal end of the housing; and a locking mechanism arranged to retain the driving mechanism in an initial inactive state in which the driving mechanism cannot be actuated; wherein when the locking mechanism is released, the driving mechanism can be actuated to push the piston towards the distal end of the housing to displace the medicament.

By using a locking mechanism to retain the driving mechanism in an initial inactive state, the driving mechanism does not need to be supported directly by other components in the injection device, including some plastic components which are prone to creeping under prolonged stress. Therefore, the phenomenon of plastic creeping causing a change of shape of the plastic components can be prevented. This increases the shelf life of the injection device. In particular, the locking mechanism can prevent any direct contact between the driving mechanism and the piston in the injection device. Therefore, the problem of prolonged pressure on the piston when an injection device is stored for a long period is prevented.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 mililiter (ml) to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 centipoise (cP) to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
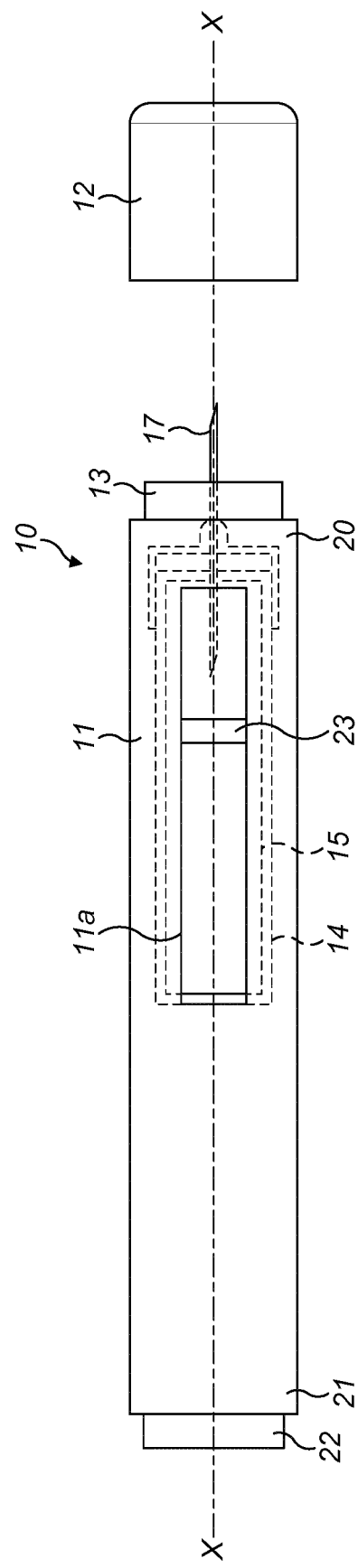

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
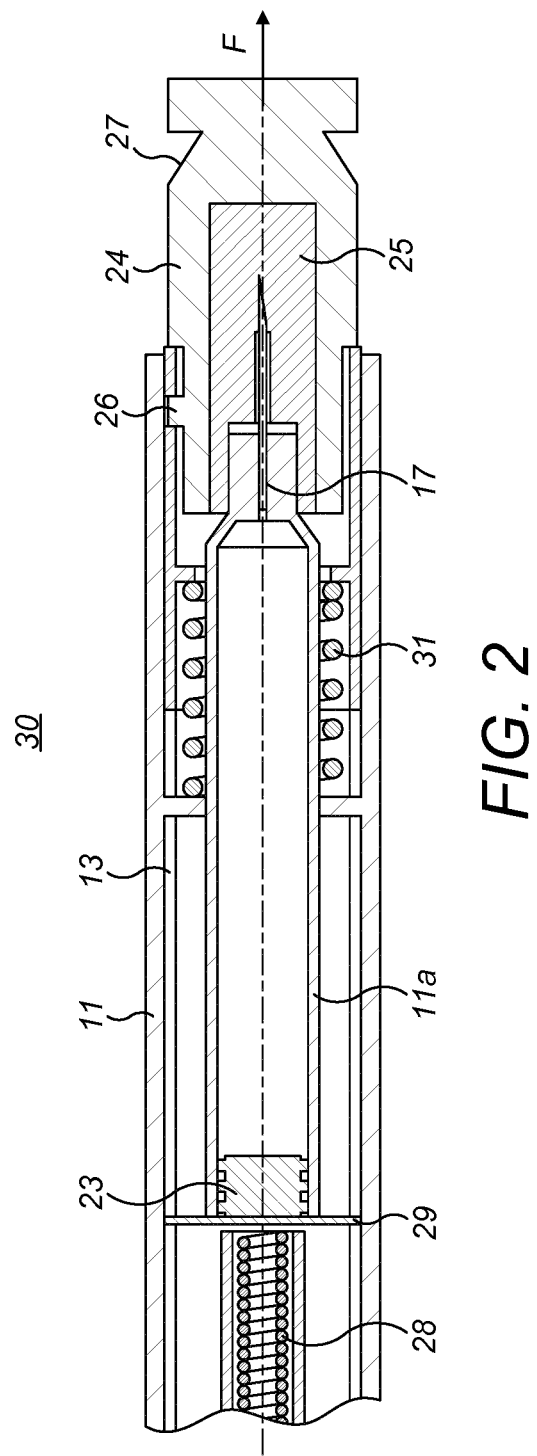
FIG. 2 is a schematic cross-sectional side view of part of an injection device according to a first state of an exemplary embodiment of the present disclosure.

Referring now to FIG. 2, part of an injection device 30 according to an exemplary embodiment is shown. The injection device 30 is in the form of an auto-injector that has similar features to the device 10 described above in relation to FIGS. 1A and 1B, with like features retaining the same reference numerals. A difference is that the cap 12 of the injection device 10 described above is omitted and is replaced with an alternative removable cap 24.

A syringe 11a is provided within the housing 11 of the injection device 30. The syringe 11a contains liquid medicament which is sealed by a piston, stopper, or bung 23 located within the syringe 11a. In an initial state, the piston 23 is positioned at a position closest to the proximal end of the housing 11. A driving mechanism 28 is provided at the proximal end of the housing 11 which is arranged to push the piston 23 towards the distal end of the housing 11 once it is in an active state and when it is actuated. The syringe 11a further includes a hollow injection needle 17 through which medicament is displaced when the piston 23 is pushed towards the distal end of the housing 11.

In the present embodiment, the driving mechanism 28 comprises a drive spring that is initially in a compressed state, storing spring energy that is to be released when the driving mechanism is actuated.

In an initial state, which will be referred to herein as the "first state", the driving mechanism 28 is held in an inactive state by a locking mechanism. In this embodiment, the locking mechanism comprises a plate member 29 which is arranged between the drive spring of the driving mechanism 28 and the piston 23 such that the drive spring of the driving mechanism 28 cannot be actuated to push the piston 23, due to the rigidity of the plate member 29. The plate meber 29 in this embodiment comprises two parts which can be separated under a pulling force. This will be explained in further detail below.

In the present embodiment, the plate member 29 is connected to an inner sleeve 13 which is arranged on an inner surface of the housing 11. Specifically, a part of the plate member 29 is connected to the inner sleeve 13 such that when the inner sleeve 13 is pulled towards the distal end of the housing 11 by a pulling force, the plate member 29 separates so as to activate the driving mechanism 28. In this embodiment, the plate member 29 of the locking mechanism becomes separated into two parts when released, such that the drive spring of the driving mechanism 28 is no long held in the inactive state. When the driving mechanism 28 is activated, it can be actuated so as to push the piston 23 towards the distal end of the housing 11.

A spring element 31 is provided within the housing 11 and arranged around the syringe 11a. The spring element 31 is initially in a compressed state when the removable cap 24 is attached to the housing 11. The spring element 31 is supported by a rib (not shown in the drawing) arranged on the inner sleeve 13 such that when the inner sleeve 31 is pulled towards the distal end, the spring element 31 decompresses due to the reduction of compressive force exerted on the spring element 31. After the removable cap 24 is disengaged from the housing 11, the inner sleeve 13 protrudes from the opening of the housing 11 under a spring force provided by the spring element 31, so as to act as a retractable needle shroud. By providing this needle shroud after the removable cap 24 is disengaged from the housing 11, the needle shroud prevents both unintentional damage of the needle during handling and access of a user to the needle for avoiding stick injuries. The needle shroud can be retracted into the housing 11, against the bias provided by the spring force, by applying a pushing force on the inner sleeve 13 towards the proximal end of the injection device, for example by applying the distal end of the injection device against a patient's skin.

The removable cap 24 of the injection device 30 of the present embodiment comprises a needle shield 25, an engagement mechanism 26, and a connection mechanism 27. The needle shield 25 comprises a recess that is configured to receive a portion of a syringe 11a that is housed in a housing 11 of the injection device 30. The friction between the needle shield and an end portion of the syringe 11a is sufficient to hold the needle shield 25 in place, covering the hollow injection needle 17.

The removable cap 24 in the first state is attached to the housing 11 such that the end portion of the syringe 11 a is received in the recess of the needle shield 25. Thus, the needle 17 is covered by the needle shield 25 to keep the needle 17 sterile and to prevent the needle 17 from causing injury to the patient.

The removable cap 24 further comprises a protrusion which in the first state is engaged with a slot provided at the inner sleeve 13 of the injection device 30. In this embodiment, the protrusion of the removable cap 24 and the slot at the inner sleeve 13 forms an engagement mechanism 26 that releasably engages the removable cap 24 with the housing 11. In this embodiment, the engagement mechanism releasably engages the removable cap 24 with the inner sleeve 13. This engagement mechanism can be disengaged by using a rotational force on the removable cap 24. This will be explained in further detail with respect to FIG. 4.

The connection mechanism 27 of the removable cap 24 is arranged to allow the removable cap 24 to be connected to an external apparatus, e.g. a tabletop apparatus.

In this embodiment, the connection mechanism 27 comprises a groove for engaging with another groove, projection, or the like at the external apparatus. The interaction between the connection mechanism 27 of the removable cap 24 and the external apparatus will be explained in further detail with respect to FIG. 9A and FIG. 9B.

Figure 3:
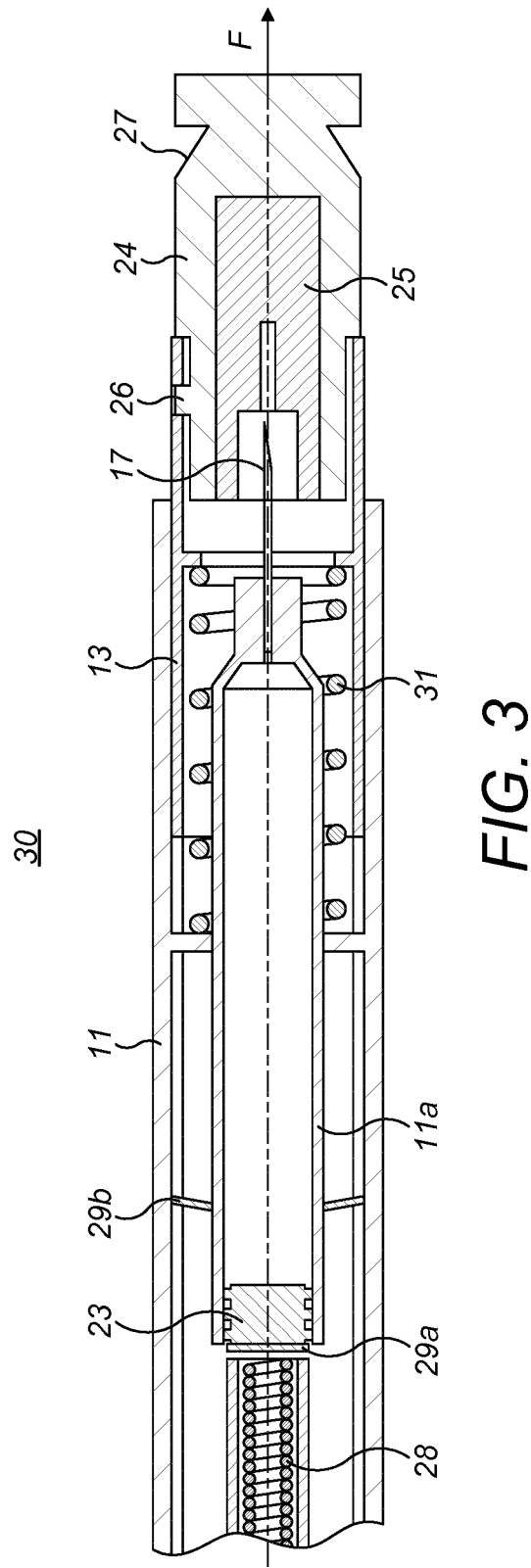
FIG. 3 is a schematic cross-sectional side view of part of the injection device of FIG. 2 in a second state.

FIG. 3 is a schematic cross-sectional side view of part of the injection device of FIG. 2 in a second state.

In the second state, i.e. an intermediate state, the removable cap 24 is pulled linearly and axially in a direction indicated by 'F' in FIG. 3, i.e. away from the proximal end of the housing 11. In this embodiment, this pulling force is applied by the external apparatus (not shown in the drawing) to which the removable cap 24 is connected.

Due to the engagement mechanism arranged between the removable cap 24 and the inner sleeve 13, as the removable cap 24 is pulled in direction 'F', the inner sleeve 13 is pulled axially together towards the same direction. However, because the engagement mechanism cannot be released unless a rotational force is applied on the removable cap 24, the removable cap 24 remains attached with the inner sleeve 13 in the second state. The spring element 31 is decompressed due to the reduction of compressive force on the spring element 31 to the inner sleeve 13, as shown in FIG. 3.

At the same time, since the inner sleeve 13 is pulled linearly and axially towards the direction 'F' (i.e. away from the proximal end of the housing 11), the plate member 29 is snapped by this pulling force which causes it to separate into two different parts 29a and 29b. The first plate part 29a remains in place between the piston 23 and the driving mechanism 28, while the second plate part 29b is attached to the inner sleeve 13 and moves along with the inner sleeve 13 as it is being pulled away from the proximal end of the housing 11.

Since the plate member 29 is separated, the driving mechanism 28 is no longer held in an inactive state. In this embodiment, the drive spring of the driving mechanism 28 is no longer held in place by the plate member 29. Therefore, the driving mechanism 28 can now be actuated by e.g. pressing a button, so as to push the piston 23 towards the distal end of the housing 11.

Figure 4:
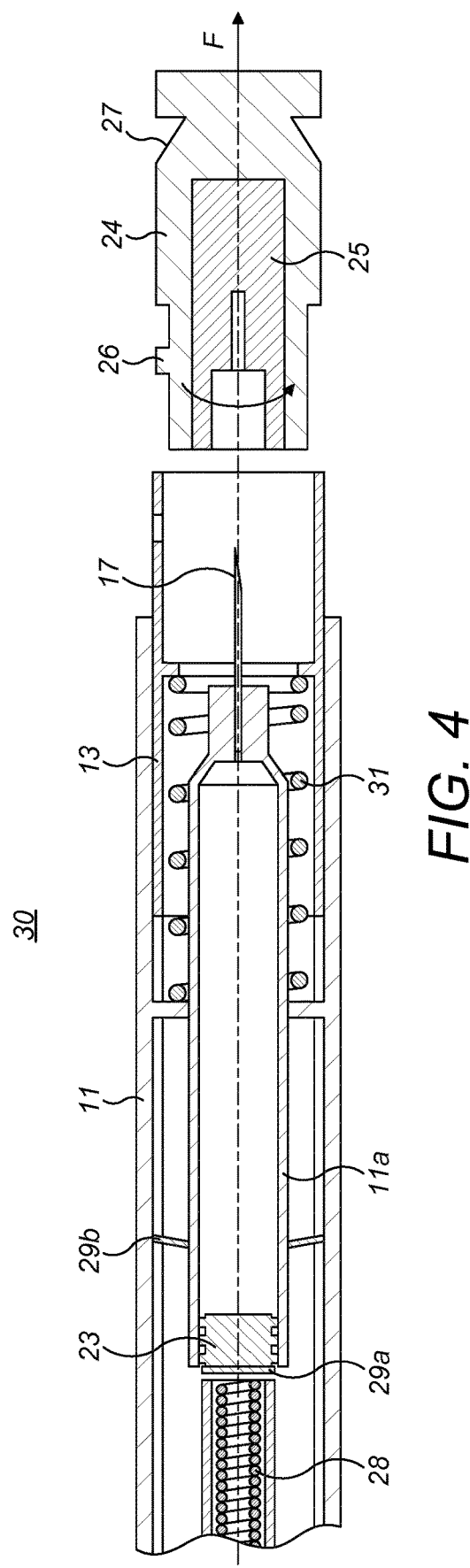
FIG. 4 is a schematic cross-sectional side view of part of the injection device of FIG. 2 in a third state.

FIG. 4 is a schematic cross-sectional side view of part of the injection device of FIG. 2 in a third state.

In the third state, i.e. a final state, the removable cap 24 is rotated in a direction as shown by the curved arrow in FIG. 4. The engagement mechanism is released by this rotational movement of the removable cap 24. Specifically, the protrusion of the removable cap 24 becomes disengaged from the slot at the inner sleeve 13 of the injection device 30 with this rotational movement. The removable cap 24 can therefore be disengaged from the rest of the injection device 30 as shown in FIG. 4.

In the third state, the inner sleeve 13 act as a retractable needle shroud to shield the needle before and after injection, since it is biased to protrude from the opening of the housing 11 by the spring force provided by the spring element 31. As explained above, by providing this needle shroud after the removable cap 24 is disengaged from the housing 11, the needle shroud prevents both unintentional damage of the needle during handling and access of a user to the needle for avoiding stick injuries.

A sequence of the operation of the injector device 30 of the present embodiment is described as follows:

The removable cap 24 is disengaged from the housing 11, either manually by a user or using an external apparatus (such as one illustrated in FIG. 7). Removal of the removable cap 24 from the housing 11 may be achieved by a user exerting a force on the removable cap 24 (in the direction of arrow 'F' in FIGS. 2 and 3) to urge the cap 24 axially away from the housing 11 and then rotating the cap 24 so as to release the engagement mechanism 26, i.e. disengaging the protrusion of the removable cap 24 from the slot at the inner sleeve 13.

Before the release of the engagement mechanism 26 (by rotating the removable cap 24), the linear axial movement of the removable cap 24 causes a linear axial movement of the inner sleeve 13. As the inner sleeve 13 moves away from the distal end of the housing 11, the plate member 29 of the locking mechanism becomes separated into two parts due to the attachment of a part of the plate member 29 to the inner sleeve 13. Therefore, the driving mechanism 28 is no longer in the inactive state and can now be actuated so as to push the piston 23. Moreover, due to the linear axial movement of the inner sleeve 13 away from the proximal end of the housing 11, the initially-tensioned spring element 31 decompresses and biases the inner sleeve 13 to protrude from the opening of the housing 11 due to the reduction of compressive force on the spring element 31. The protruding inner sleeve 13 from the housing 11 acts as a retractable needle shroud to prevent needle stick injuries or unintentional damage to the needle 17.

To inject medicament, the user grabs the injection device 30 with their whole hand and pushes the distal end of the injection device 30 against the injection site. As the user exerts pressure on the inner sleeve 13 by applying it against the injection site, the inner sleeve 13 retracts into the housing 11 against the bias provided by the spring element 31 so as to fully expose the needle 17 for injection. After the needle 17 has been inserted into the injection site, the user then acts on the actuator (not shown in the drawings) which activates the driving mechanism 28. The drive spring of the driving mechanism 28 releases and decompresses so as to exert a force on the piston 23 towards the distal end of the housing 11 to inject medicament contained in the syringe 11a.

Figure 5A:
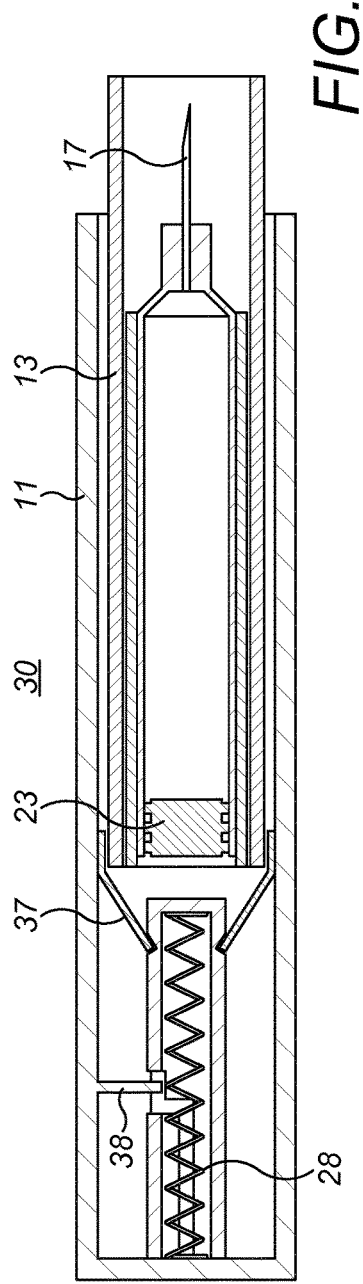
FIG. 5A is a schematic cross-sectional side view of an injection device according to a first state of another exemplary embodiment of the present disclosure.
Figure 5B:
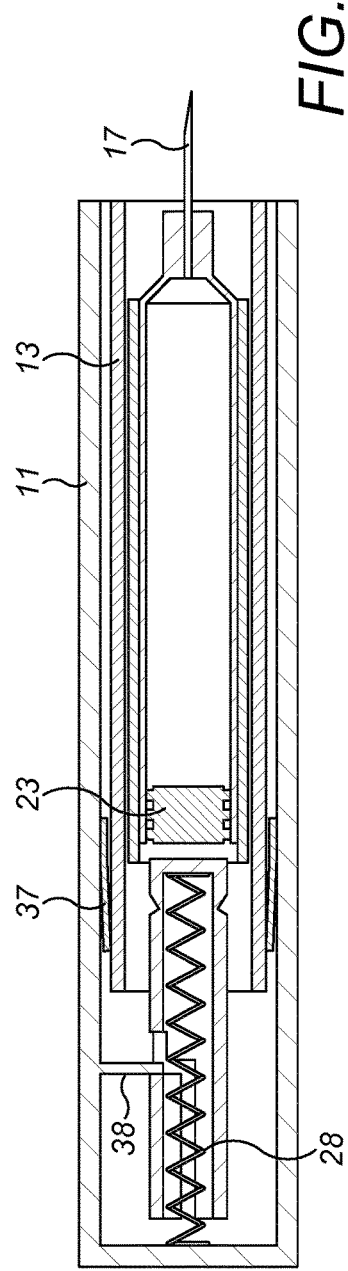
FIG. 5B is a schematic cross-sectional side view of the injection device of FIG. 5A in a second state.
Figure 5C:
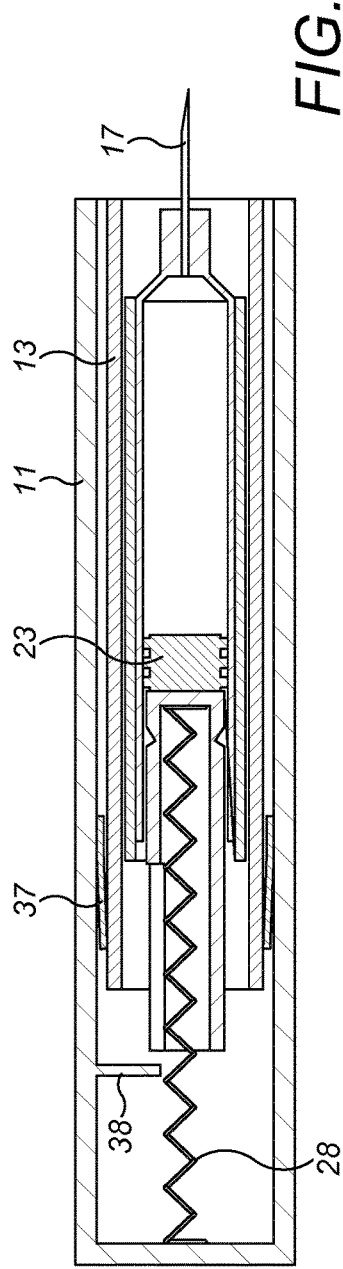
FIG. 5C is a schematic cross-sectional side view of the injection device of FIG. 5A in a third state.

FIGS. 5A to 5C are schematic cross-sectional side views of an injection device according to another exemplary embodiment in a first state, a second state, and a third state, respectively.

Referring to FIGS. 5A to 5C, an injection device 30 according to a different embodiment is shown. The injection device 30 is in the form of an auto-injector that has similar features to that shown in FIG. 2, with like features retaining the same reference numerals. A difference between the injection device 30 of FIG. 5A and the injection device of FIG. 2 is the locking mechanism comprises a clamp 37 for retaining the driving mechanism 28 in an initial inactive state in a first state of the injection device 30. A rib 38 is provided on an inner surface of the housing 11 for holding the driving mechanism after the locking mechanism is related and before actuation of the driving mechanism, as will be explained in more detail below.

In the present embodiment, the driving mechanism comprises a drive spring that is initially in a compressed state, storing spring energy that is to be released when the driving mechanism is actuated. The driving mechanism further comprises a housing member which is arranged to house the drive spring and is arranged to move towards the distal end of the housing 11 when the driving mechanism is actuated.

In the first state, the driving mechanism 28 is held in an inactive state by the locking mechanism, which comprises the clamp 37. In this embodiment, the clamp 37 is arranged to clamp onto the housing member which houses the drive spring such that the driving mechanism 28 cannot be actuated to push the piston 23.

In the present embodiment, the clamp 37 of the locking mechanism is arranged within the housing 11 such that when the inner sleeve 13 is pushed towards the proximal end of the housing 11 by a pushing force (e.g. when the opening of the housing 11 is applied against a patient's skin, or by use of a tabletop apparatus), the inner sleeve 13 pushes against the clamp 37 and bends the clamp 37, as shown in the second state in FIG. 5B, so as to release the locking mechanism which in turn activates the driving mechanism 28. As shown in FIG. 5B, when the locking mechanism is released, a part of the housing member of the driving mechanism 28 is held against the rib 38. The rib 38 can then be actuated, for example by means of a push button, so as to release the housing member of the driving mechanism 28 to push the piston 23 towards the distal end of the housing 11, as illustrated in the third states in FIG. 5C.

As a result, a two-step operation is required in order to actuate the driving mechanism in this embodiment. In the first step, the user is required to bend the clamp 37 by way of for example applying the opening of the housing 11 against a patient's skin so as to activate the driving mechanism. In the second step, the user is required to actuate the rib 38 by means of for example a push button so as to release the housing member of the driving mechanism to push the piston 23.

Figure 6A:
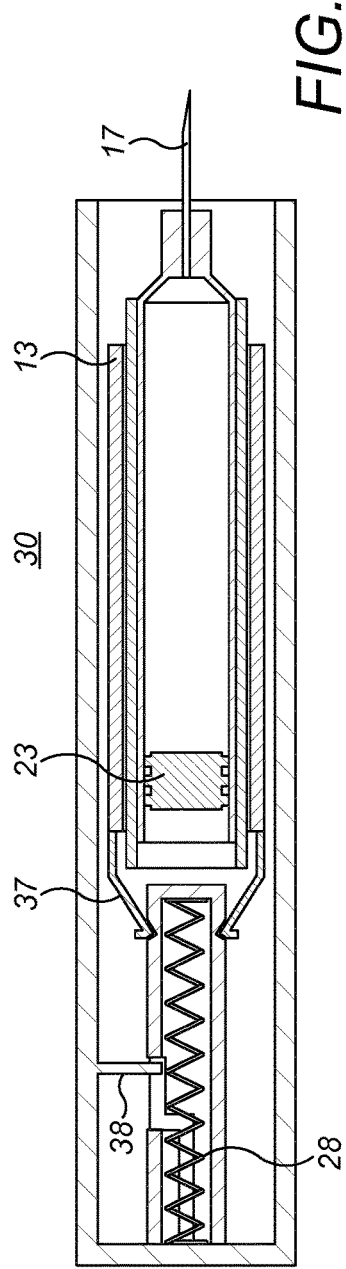
FIG. 6A is a schematic cross-sectional side view of an injection device according to a first state of another exemplary embodiment of the present disclosure.
Figure 6B:
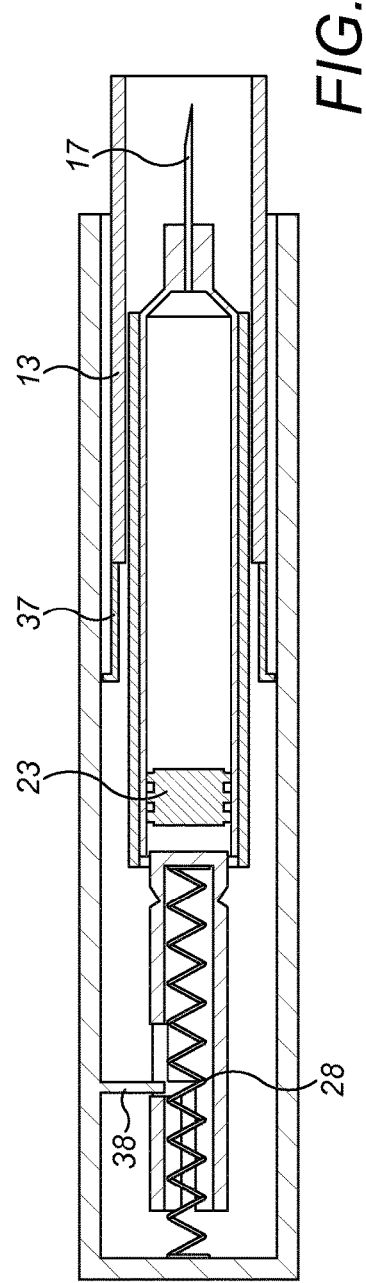
FIG. 6B is a schematic cross-sectional side view of the injection device of FIG. 6A in a second state.
Figure 6C:
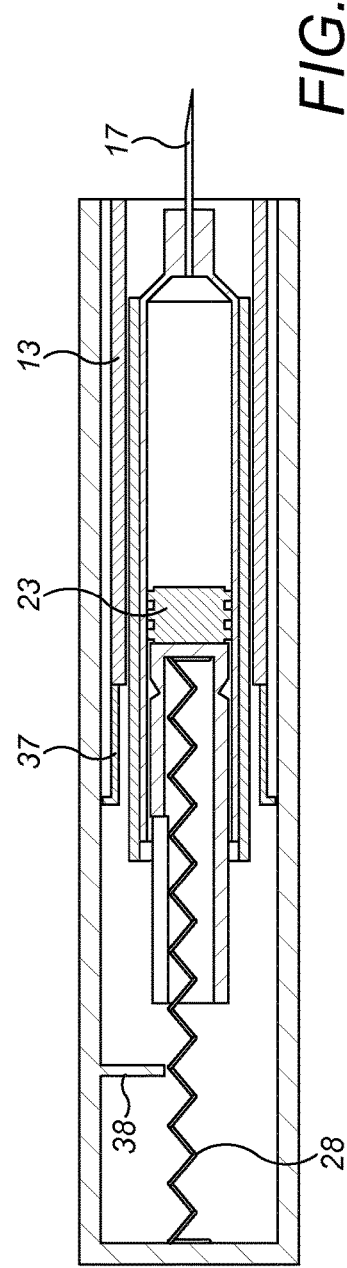
FIG. 6C is a schematic cross-sectional side view of the injection device of FIG. 6A in a third state.

FIGS. 6A to 6C are schematic cross-sectional side views of an injection device according to another exemplary embodiment in a first state, a second state, and a third state, respectively.

Referring to FIGS. 6A to 6C, an injection device 30 according to a different embodiment is shown. The injection device 30 is in the form of an auto-injector that has similar features to that shown in FIG. 2, with like features retaining the same reference numerals. A difference between the injection device 30 of FIG. 6A and the injection device of FIG. 2 is the locking mechanism comprises a clamp 37 for retaining the driving mechanism 28 in an initial inactive state in a first state of the injection device 30. A rib 38 is provided on an inner surface of the housing 11 for holding the driving mechanism after the locking mechanism is related and before actuation of the driving mechanism, as will be explained in more detail below.

In the present embodiment, the driving mechanism comprises a drive spring that is initially in a compressed state, storing spring energy that is to be released when the driving mechanism is actuated. The driving mechanism further comprises a housing member which is arranged to house the drive spring and is arranged to move towards the distal end of the housing 11 when the driving mechanism is actuated.

In the first state, the driving mechanism 28 is held in an inactive state by the locking mechanism, which comprises the clamp 37. In this embodiment, the clamp 37 is arranged to clamp onto the housing member housing the drive spring such that the driving mechanism 28 cannot be actuated to push the piston 23.

In the present embodiment, the clamp 37 of the locking mechanism is arranged within the housing 11 and fixedly connected to the inner sleeve 13. When the inner sleeve 13 moves towards the distal end of the housing 11 due to the reduction of compressive force as the removable cap (not shown in this drawing) is being disengaged from the housing 11, the clamp 37 becomes bent due to its connection to the inner sleeve 13, as shown in FIG. 6B, so as to release the locking mechanism which in turn activates the driving mechanism 28. As shown in FIG. 6B, when the locking mechanism is released, a part of the housing member of the driving mechanism 28 is held against the rib 38. The rib 38 can be actuated, for example by means of a push button, so as to release the housing member of the driving mechanism 28 to push the piston 23 towards the proximal end of the housing 11, as illustrated in the third states in FIG. 6C.

In this embodiment, similarly a two-step operation is required in order to actuate the driving mechanism. In the first step, the user is required to bend the clamp 37 by way of for example disengaging the removable cap from the housing to move the inner sleeve towards the distal end of the injection device, so as to activate the driving mechanism. In the second step, the user is required to actuate the rib 38 by means of for example a push button so as to release the housing member of the driving mechanism to push the piston 23.

Figure 7A:
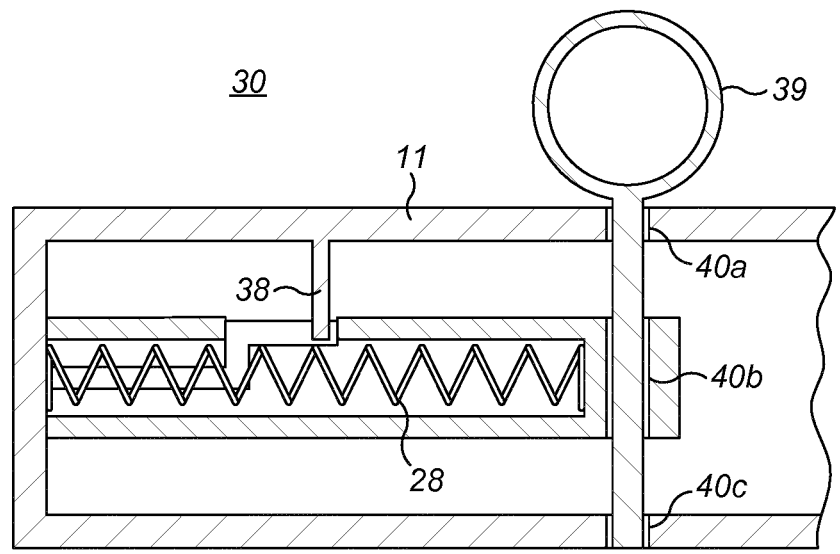
FIG. 7A is a schematic cross-sectional side view of part of an inject device according to a first state of another exemplary embodiment of the present disclosure.
Figure 7B:
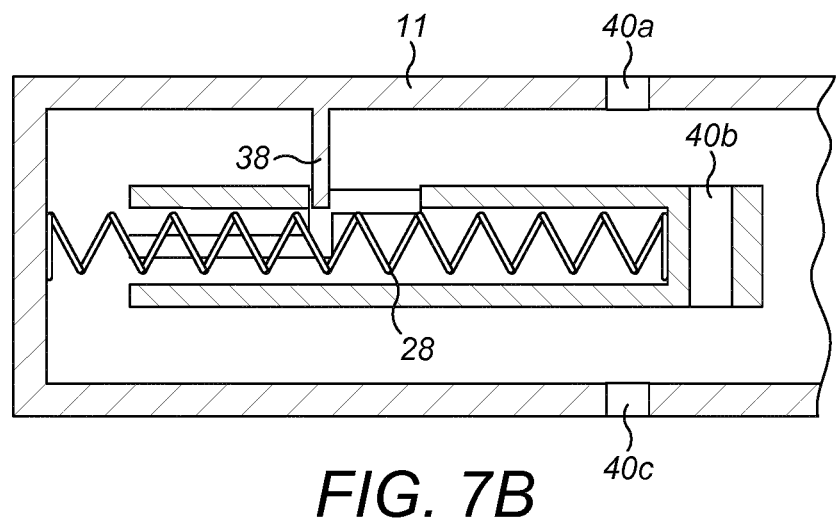
FIG. 7B is a schematic cross-sectional side view of part of the injection device of FIG. 7A in a second state.

FIGS. 7A and 7B are schematic cross-sectional side views of a part of an injection device according to another exemplary embodiment in a first state and a second state respectively.

Referring to FIGS. 7A and 7B, a part of an injection device 30 according to a different embodiment is shown. The injection device 30 is in the form of an auto-injector that has similar features to that shown in FIG. 2, with like features retaining the same reference numerals. A difference between the injection device 30 of FIG. 7A and the injection device of FIG. 2 is a cotter 39, first through-hole 40a, second through-hole 40b, and third through-hole 40c together form the locking mechanism for retaining the driving mechanism 28 in an inactive state in a first state of the injection device 30. A rib 38 is provided on an inner surface of the housing 11 for holding the driving mechanism after the locking mechanism is related and before actuation of the driving mechanism, as will be explained in more detail below.

In the present embodiment, the driving mechanism comprises a drive spring that is initially in a compressed state, storing spring energy that is to be released when the driving mechanism is actuated. The driving mechanism further comprises a housing member which is arranged to house the drive spring and is arranged to move towards the distal end of the housing 11 when the driving mechanism is actuated.

In the first state, the driving mechanism 28 is held in an inactive state by the locking mechanism, which comprises the cotter 39 and the first, second, and third through-holes 40a, 40b, 40c. As shown in FIG. 7A, in the first state the cotter 39 is removably inserted through the first, second, and third through-holes 40a, 40b, 40c, which are respectively positioned at a first side of the housing 11, the housing member of the driving mechanism 28, and a second side of the housing 11 which is opposite to the first side. The first, second, and third through-holes 40a, 40b, 40c are configured to be aligned with each other such that the cotter 39 can be removably inserted through the housing 11 in a direction perpendicular to the longitudinal axis of the injection device 30. In the first state, as the cotter 39 is engaged with the first, second, and third through-holes 40a, 40b, 40c, the driving mechanism 28 is held in place at the proximal end of the injection device 30. Specifically, the housing member of the driving mechanism 29 is held in place in the inactive state by the presence of the cotter 39 through the second through-hole 40b at the housing member. Therefore, in the first state, the driving mechanism 28 cannot be actuated to push the piston (not shown in the drawing).

The locking mechanism can be released by removing the cotter 39 from the first, second, and third through-holes 40a, 40b, 40c. When the locking mechanism is released, the housing member of the driving mechanism 28 is no longer held at the proximal end of the housing 11 and therefore the driving mechanism 28 becomes activated. As shown in FIG. 7B, when the locking mechanism is released, a part of the housing member of the driving mechanism 28 is held against the rib 38. The rib 38 can be actuated, for example by means of a push button, so as to release the housing member of the driving mechanism 28 to push the piston (not shown in this drawing) towards the distal end of the housing 11 to displace medicament.

Figure 8:
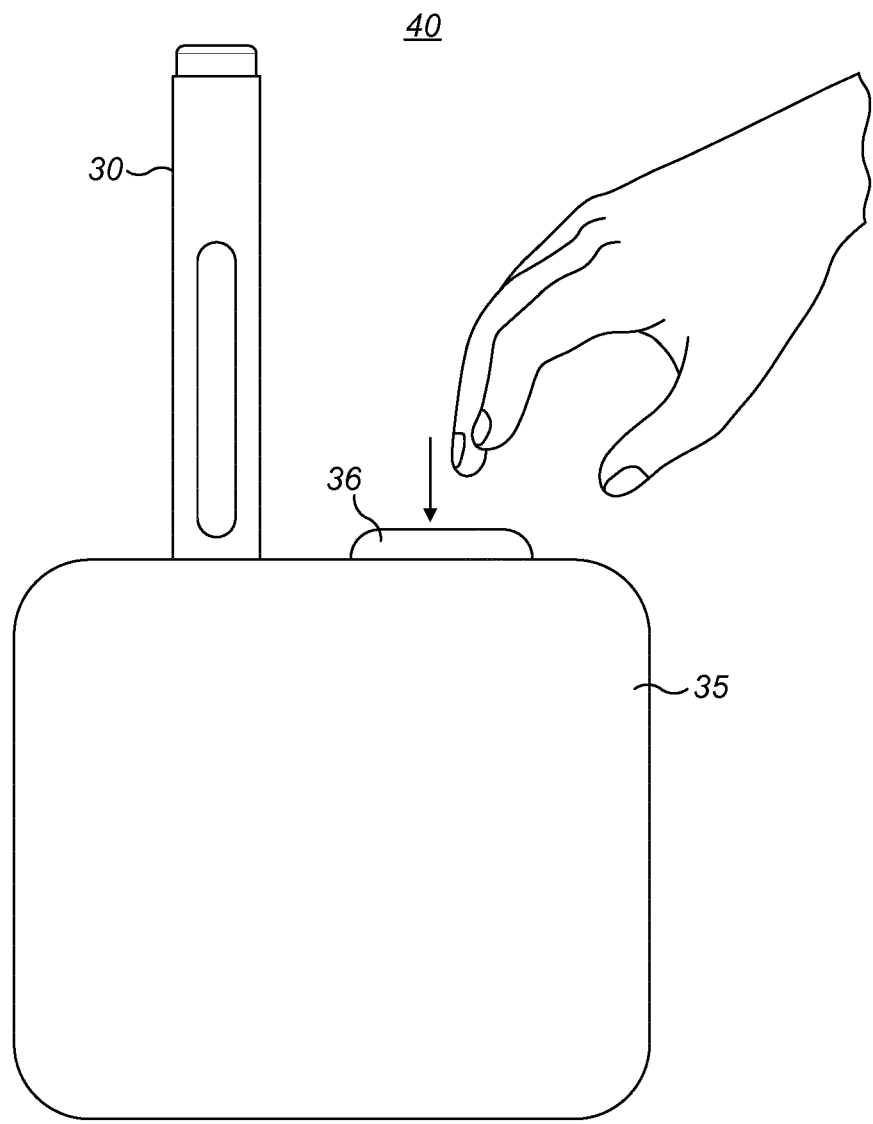
FIG. 8 illustrates a system comprising an injection device and a tabletop apparatus, according to another exemplary embodiment of the present disclosure.

FIG. 8 is a system comprising an injection device and a tabletop apparatus, according to another exemplary embodiment.

As shown in FIG. 8, the system 40 comprises an injection device 30 and a tabletop apparatus 25. The injection device 30 is as described with respect to FIGS. 2 to 4. The tabletop apparatus 35 comprises a button 36 which is positioned at an upper surface of the apparatus 35. The tabletop apparatus 35 in this embodiment is configured to remove the removable cap 24 from the injection device 30.

The tabletop apparatus 35 is an example of an external apparatus at which the removable cap 24 of the injector device 30 as illustrated in FIGS. 2 to 4 can be engaged. Specifically, the connection mechanism 27 of the removable cap 24 as illustrated in FIGS. 2 to 4 can be connected to the tabletop apparatus 35 in the manner shown in FIG. 8, i.e. vertically connected with the upper surface of the tabletop apparatus 35. An interface (not shown) is provided at the upper surface of the tabletop apparatus 35, the interface comprises a movable projection which engages with (e.g. grips) the connection mechanism 27 of the removable cap 24.

The button 36 of the tabletop apparatus 35 is configured such that when it is pressed, the movable projection acts on the connection mechanism 27 of the removable cap 24 such that the removable cap 24 is moved axially away from the housing 11 and rotated to release the engagement mechanism. The removable cap 24 is therefore removed simply by a press of the button 36 of the tabletop 35. At the same time, the axial movement of the removable cap 24 causes an axial movement of the inner sleeve 13 of the injection device 30, which in turn causes the plate member 29 to become separated into different parts. The driving mechanism 28 is therefore no longer in an inactive state and can be actuated to push the piston to displace medicament.

The use of the tabletop apparatus 35 can therefore reduce the required force to remove the removable cap 24 from the injection device 30 as well as the required force to separate the plate member 29 so as to activate the driving mechanism 28.

A sequence of operation of the system 40 as illustrated in FIG. 8 is described as follows:

The injection device 30 is first engaged with the interface on the upper surface of the tabletop apparatus 35 such that the connection mechanism 27 of the removable cap 24 is engaged with the movable projection at the interface. The movable projection grips at the connection mechanism 27, and when the user presses the button 36 of the tabletop apparatus 35, the movable projection acts on the connection mechanism 27 so as to pull the removable cap 24 axially away from the housing 11.

This linear and axial movement of the removable cap 24 causes a linear and axial movement of the inner sleeve 13 of the injection device 30. As the inner sleeve 13 moves away from the proximal end of the housing 11, the plate member 29 becomes separated (due to the attachment of mechanism part of the plate member 29 to the inner sleeve 13) so as to release the driving mechanism 28. In other words, the driving mechanism 28 is no longer in the inactive state and can now be actuated so as to push the piston 23.

Immediately afterwards, the movable projection also acts on the connection mechanism 27 to rotate the removable cap 24. This releases the engagement mechanism, i.e. disengages the protrusion 26 of the removable cap 24 from the slot at the inner sleeve 13. As the removable cap 24 is being disengaged from the rest of the injection device 30, the inner sleeve 13 protrudes from the opening of the housing 11 due to the reduction of compressive force exerted on the inner sleeve 13. After the removable cap 24 is disengaged from the housing 11, the inner sleeve 13 protrudes from the opening of the housing 11 so as to act as a retractable needle shroud. By providing this needle shroud after the removable cap 24 is disengaged from the housing 11, the needle shroud prevents both unintentional damage of the needle during handling and access of a user to the needle for avoiding stick injuries.

To inject medicament, the user grabs the injection device 30 with their whole hand, removes it from the tabletop apparatus 35, and pushes the distal end of the injection device 30 against the injection site which causes the inner sleeve 13 to retract into the housing 11 and exposing the needle 17. After the needle 17 has been inserted into the injection site, the user then acts on the actuator (not shown in the drawings) which activates the driving mechanism 28. The drive spring of the driving mechanism 28 releases and decompresses so as to exert a force on the piston 23 towards the distal end of the housing 11 to inject medicament contained in the syringe 11a.

Figure 9B:
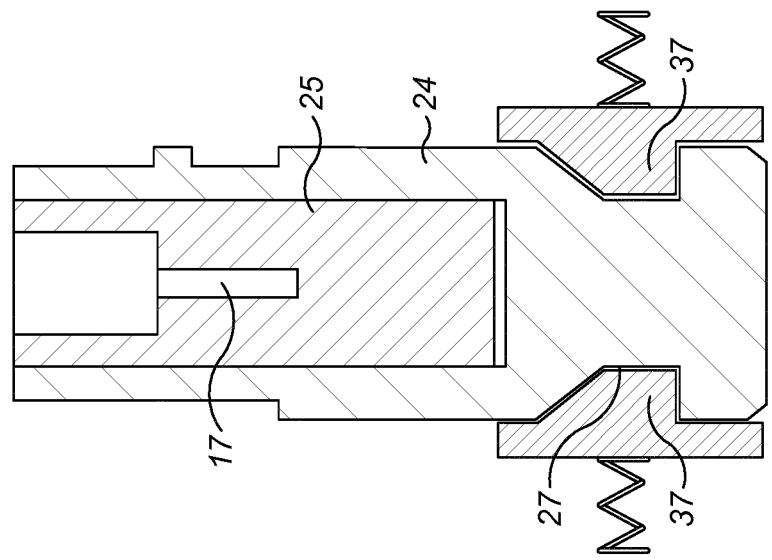
FIGS. 9A and 9B are schematic cross-sectional views illustrating interaction between part of the removable cap of FIG. 2 and part of the tabletop apparatus of FIG. 8.
Figure 9A:
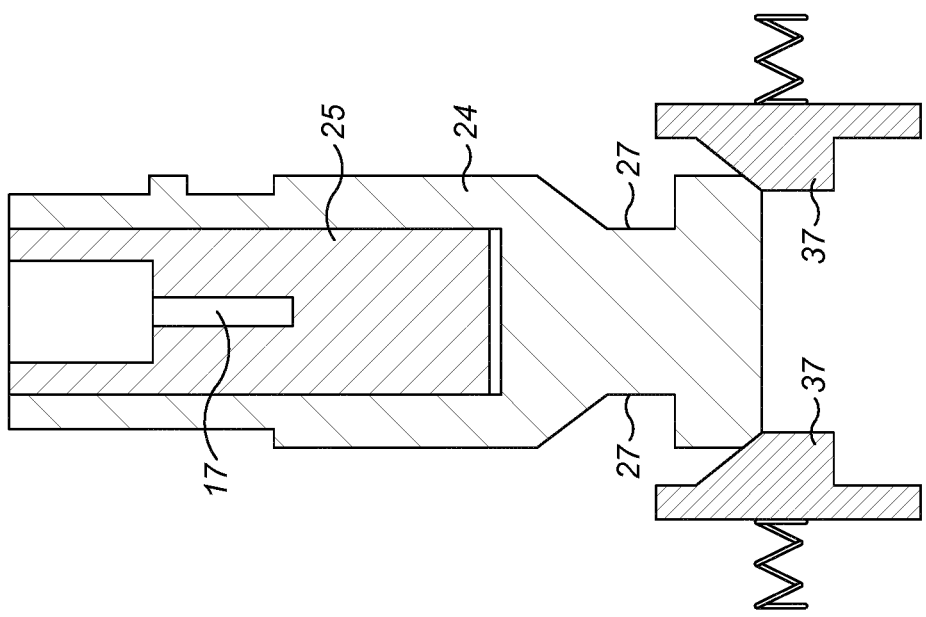

FIGS. 9A and 9B are schematic cross-sectional views illustrating interaction between part of the removable cap of FIG. 2 and part of the tabletop apparatus of FIG. 8.

As shown in FIGS. 9A and 9B, a connection mechanism 27 is provided at the removable cap 24, the connection mechanism 27 being arranged to be engaged with the tabletop apparatus 25. In this embodiment, the connection mechanism 27 comprises a groove for engaging with a projection 37 at the tabletop apparatus 35. Specifically, the connection mechanism 27 of the removable cap 24 can be vertically engaged with the upper surface of the tabletop apparatus 35 through the engagement between the groove and the protrusion. In this embodiment, the projections 37 are positioned at an interface of the tabletop apparatus 35 and is arranged to be movable so as to receive the connection mechanism 27. The interface at the tabletop apparatus 35 also comprises a recess to receive at least a part of the removable cap 24.

Spring elements are provided around the movable projections 37 such that when the removable cap 24 is pushed against the interface of the tabletop apparatus 35 vertically, the movable projections 37 move apart, as shown in FIG. 9B, to allow accommodation of a part of the removable cap 24 and the engagement between the connection mechanism 27 and the movable projections 37. Furthermore, the movable projections 37 may also be configured such that they can move apart when an actuation member (not shown in the drawing) is actuated. For example, an additional push button may be provided at the tabletop apparatus 35 such that when the button is pushed, the movable projections 37 move apart to allow the removable cap 24 to be disengaged with the tabletop apparatus 35.

Although it is described above that a pulling force on the removable cap is applied by an external apparatus, in alternative embodiments the pulling force may be applied manually by a user.

Although it is described above that the tabletop device is used in connection with the injection device as illustrated in FIGS. 2 to 4, in alternative embodiments, the tabletop apparatus may be used in connection with the injection devices as illustrated in the other drawings (FIGS. 5 to 7). For example, the tabletop device may be configured such that when the injection device as illustrated in FIGS. 5A to 5C is mounted onto the tabletop device, it is capable of pushing the inner sleeve of the injection device towards the proximal end so as to bend the clamp in the injection device. In this example, the tabletop apparatus may comprise a hollow cylinder-shaped member so as to push the inner sleeve towards the proximal end of the injection device.

In alternative embodiments, the protrusion at the removable cap may be replaced by a slot and the slot at the inner sleeve by the replaced by a protrusion. The principle of the engagement mechanism in these embodiments remains the same, i.e. unlocking by rotating the removable cap.

In alternative embodiments, instead of configuring the inner sleeve and the locking mechanism such that when the inner sleeve is pulled away from the housing, the plate member is separated into different parts, the inner sleeve may be arranged such that when it is pushed into the housing, it causes the plate member mechanism to be separated so as to activate the driving mechanism.

In alternative embodiments, the injection device may not comprise a retractable inner sleeve. In these alternative embodiments, automatic needle insertion technology may be used at the injection device. In these alternative embodiments, the locking mechanism may be coupled with the removable cap or an additional user element, such as a slider or a button.

In alternative embodiments, a lever may be provided at the tabletop apparatus instead of the push button. The lever may be configured such that when it is actuated, the movable projection acts on the connection mechanism of the removable cap such that the removable cap is moved axially away from the housing of the injection device and rotated to release the engagement mechanism.

In alternative embodiments, an electronic tabletop apparatus may be provided which comprises a recess, an interface, and an electronic engaging unit configured to engage with the connection mechanism of the removable cap and to remove the cap by moving and rotating the removable cap axially away from the housing of the injection device.

Although claims have been formulated in this application to particular combinations of features, it should be understood that the scope of the disclosure also includes any novel features or any novel combinations of features disclosed herein either explicitly or implicitly or any generalization thereof, whether or not it relates to the same invention as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Those skilled in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta-¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injection device comprising:
    a housing arranged to contain a syringe with a piston for sealing the syringe and displacing a medicament, the housing having a proximal end and a distal end, wherein the distal end is configured to be applied against an injection site;
    a driving mechanism comprising a drive spring, the driving mechanism being arranged between the piston and the proximal end of the housing;
    a locking mechanism comprising a clamp, the locking mechanism being arranged to retain the driving mechanism in an initial inactive state at which direct contact between the driving mechanism and the piston is prevented and the driving mechanism is not actuatable;
    a retractable inner sleeve;
    a removable cap arranged to be removably engaged with the distal end of the housing; and
    an engagement mechanism configured to releasably engage the removable cap with the retractable inner sleeve, wherein the engagement mechanism comprises a protrusion at an external surface of the removable cap and a slot at an inner surface of the retractable inner sleeve, wherein the protrusion is arranged to be releasably engaged with the slot by rotation of the removable cap.

2. The injection device of claim 1, wherein the clamp is arranged to clamp a housing member of the driving mechanism in a fixed position in the initial inactive state, wherein the clamp is arranged to be released by a pulling force to release the housing member so that the driving mechanism gets actuated.

3. The injection device of claim 2, wherein the retractable inner sleeve is located adjacent to the clamp, wherein the clamp is connected to the retractable inner sleeve and the pulling force is provided by pulling the retractable inner sleeve in a distal direction of the injection device.

4. The injection device of claim 1, wherein the injection device contains a liquid medicament.

5. The injection device of claim 1, wherein the driving mechanism comprises a housing member which houses the drive spring, the drive spring being in a compressed state when the driving mechanism is in the initial inactive state, and wherein the drive spring is configured to decompress when the locking mechanism is released so as to push the piston towards the distal end of the housing.

6. The injection device of claim 1, wherein the clamp is arranged to clamp a housing member of the driving mechanism in a fixed position in the initial inactive state, wherein the clamp is arranged to be bent by a pushing force to release the housing member so that the driving mechanism gets actuated.

7. An injection device comprising:
    a housing arranged to contain a syringe with a piston for sealing the syringe and displacing a medicament, the housing having a proximal end and a distal end, wherein the distal end is configured to be applied against an injection site;
    a driving mechanism arranged between the piston and the proximal end of the housing;
    a locking mechanism comprising a clamp, the locking mechanism being arranged to retain the driving mechanism in an initial inactive state at which direct contact between the driving mechanism and the piston is prevented and the driving mechanism is not actuatable,
    wherein the driving mechanism comprises a drive spring and a housing member which houses the drive spring, the drive spring being in a compressed state when the driving mechanism is in the initial inactive state, and wherein the drive spring is configured to decompress when the locking mechanism is released so as to push the piston towards the distal end of the housing; and a rib arranged on an inner surface of the housing, wherein the rib is arranged to hold at least a part of the housing member of the driving mechanism when the locking mechanism is released, the rib being further arranged to be actuated so as to release the housing member of the driving mechanism to push the piston towards the distal end.

8. The injection device of claim 7, further comprising:
a retractable inner sleeve; and
a removable cap arranged to be removably engaged with the distal end of the housing, and an engagement mechanism to releasably engage the removable cap with the retractable inner sleeve, wherein the engagement mechanism comprises a protrusion at an external surface of the removable cap and a slot at an inner surface of the retractable inner sleeve, wherein the protrusion is arranged to be releasably engaged with the slot by rotation of the removable cap.

9. The injection device of claim 7, wherein the clamp is arranged to clamp the housing member of the driving mechanism in a fixed position in the initial inactive state, wherein the clamp is arranged to be bent by a pushing force to release the housing member so that the driving mechanism gets actuated.

10. The injection device of claim 7, wherein the clamp is arranged to clamp the housing member of the driving mechanism in a fixed position in the initial inactive state, wherein the clamp is arranged to be released by a pulling force to release the housing member so that the driving mechanism gets actuated.

11. The injection device of claim 10, further comprising a retractable inner sleeve located adjacent to the clamp, wherein the clamp is connected to the retractable inner sleeve and the pulling force is provided by pulling the retractable inner sleeve in a distal direction of the injection device.

12. The injection device of claim 7, wherein the injection device contains a liquid medicament.

13. An injection device comprising:
a housing arranged to contain a syringe with a piston for sealing the syringe and displacing a medicament, the housing having a proximal end and a distal end, wherein the distal end is configured to be applied against an injection site;

a driving mechanism comprising a drive spring, the driving mechanism being arranged between the piston and the proximal end of the housing;

a locking mechanism comprising a clamp, the locking mechanism being arranged to retain the driving mechanism in an initial inactive state at which direct contact between the driving mechanism and the piston is prevented and the driving mechanism is not actuatable, wherein the clamp is arranged to clamp a housing member of the driving mechanism in a fixed position in the initial inactive state, wherein the clamp is arranged to be bent by a pushing force to release the housing member so that the driving mechanism gets actuated; and a retractable inner sleeve located adjacent to the clamp, wherein the pushing force is provided by pushing the retractable inner sleeve in a proximal direction of the injection device.

14. The injection device of claim 13, further comprising:
p1 a removable cap arranged to be removably engaged with the distal end of the housing, and an engagement mechanism to releasably engage the removable cap with the retractable inner sleeve, wherein the engagement mechanism comprises a protrusion at an external surface of the removable cap and a slot at an inner surface of the retractable inner sleeve, wherein the protrusion is arranged to be releasably engaged with the slot by rotation of the removable cap.

15. The injection device of claim 13, wherein the housing member houses the drive spring, the drive spring being in a compressed state when the driving mechanism is in the initial inactive state, and wherein the drive spring is configured to decompress when the locking mechanism is released so as to push the piston towards the distal end of the housing.

16. The injection device of claim 15, further comprising a rib arranged on an inner surface of the housing, wherein the rib is arranged to hold at least a part of the housing member of the driving mechanism when the locking mechanism is released, the rib being further arranged to be actuated so as to release the housing member of the driving mechanism to push the piston towards the distal end.

17. The injection device of claim 13, wherein the injection device contains a liquid medicament.

* * * * *

UNITED STATES PATENT AND TRADEMARK OFFICE
CERTIFICATE OF CORRECTION

PATENT NO. : 11,351,304 B2
APPLICATION NO. : 16/328523
DATED : June 7, 2022
INVENTOR(S) : Wendland et al.

It is certified that error appears in the above-identified patent and that said Letters Patent is hereby corrected as shown below:

In the Claims

Column 22, Line 22, Claim 14, delete "p1 a" and insert -- a --

Signed and Sealed this
Nineteenth Day of July, 2022

Katherine Kelly Vidal
*Director of the United States Patent and Trademark Office*